United States Patent [19]
Dunigan et al.

[11] Patent Number: 6,099,707
[45] Date of Patent: *Aug. 8, 2000

[54] APPARATUS FOR SENSING OXYGEN CONCENTRATION

[75] Inventors: Francis X. Dunigan, Thorndale; Edward C. Berdich, Downingtown; Peter M. Draper, Honeybrook, all of Pa.

[73] Assignee: DOXS Technology Systems, Inc, Downingtown, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/620,944

[22] Filed: Mar. 22, 1996

[51] Int. Cl.$^7$ .................................................. G01N 27/404
[52] U.S. Cl. .................. 204/406; 204/415; 204/431; 204/432; 205/783
[58] Field of Search ................... 204/406, 415, 204/431, 432

[56] References Cited

U.S. PATENT DOCUMENTS

| | | | |
|---|---|---|---|
| 2,861,926 | 11/1958 | Jacobson | 204/432 |
| 2,913,386 | 11/1959 | Clark | 204/415 |
| 2,939,827 | 6/1960 | Jacobson et al. | 204/432 |
| 2,991,412 | 7/1961 | Kordesch | 204/432 |
| 3,410,778 | 11/1968 | Krasberg | 204/415 |
| 3,556,098 | 1/1971 | Kanwisher | 204/415 |
| 3,718,563 | 2/1973 | Krull et al. | 204/415 |
| 4,062,750 | 12/1977 | Butler | 204/415 |
| 4,132,616 | 1/1979 | Tantram et al. | 204/415 |
| 4,207,514 | 6/1980 | Klein | 320/134 |
| 4,661,759 | 4/1987 | Klein | 320/134 |
| 4,735,691 | 4/1988 | Green et al. | 204/406 |
| 4,913,983 | 4/1990 | Cheiky | 429/13 |
| 5,185,218 | 2/1993 | Brokman et al. | 429/27 |
| 5,387,477 | 2/1995 | Cheiky | 426/26 |
| 5,429,885 | 7/1995 | Stockburger et al. | 429/13 |
| 5,445,901 | 8/1995 | Korall et al. | 429/27 |
| 5,487,955 | 1/1996 | Korall et al. | 429/26 |

FOREIGN PATENT DOCUMENTS

| | | |
|---|---|---|
| 153155 | 9/1983 | Japan . |
| 200157 | 11/1983 | Japan . |
| 26053 | 2/1984 | Japan . |

OTHER PUBLICATIONS

"Anesthesia Units", Emergency Care Research Institute, Product Comparison Report [10–134] (Jul. 1996.

"Requirements for Oxygen Analyzers for Monitoring Patient Breathing Mixtures", American National Standards Institute, Inc., ANSI 279.10–1979 (1979), month unavailable.

*Primary Examiner*—T. Tung
*Attorney, Agent, or Firm*—Howson & Howson

[57] ABSTRACT

An apparatus and method for sensing a concentration of oxygen in a flow of gas in a breathing circuit for a patient. A biasing voltage is provided across a zinc-air cell so that the zinc-air cell produces a current having a magnitude, wherein the magnitude of the current corresponds to the concentration of oxygen in the gas.

6 Claims, 4 Drawing Sheets

APPARATUS FOR SENSING OXYGEN CONCENTRATION

BACKGROUND OF THE INVENTION

1. Field of the Invention

The present invention relates to oxygen sensors.

2. Description of the Related Art

The exposure of hospital patients to infectious agents introduced by other patients is one of the most significant dangers in modern hospitals. As a result, hospitals have recently focused a great deal of energy on the prevention of such cross-contamination between patients. One problem in eliminating the danger of cross-contamination lies in the oxygen sensors currently employed in a variety of medical devices, such as anesthesia and ventilator circuits, aerosol tents, and the like. As will be understood, "breathing circuit" as used herein refers to a (non-electronic) circuit for carrying a flow of a gas.

Existing oxygen sensors typically employ a non-disposable, reusable galvanic cell for sensing changes in oxygen concentration. Existing galvanic oxygen sensors are based on the cathodic reduction of molecular oxygen at the working electrode and an oxidation reaction at the sacrificial anode. An example of the galvanic type cell is a cell made of a silver working electrode and a lead sacrificial anode with a KOH supporting electrolyte. These cells are typically self-powered.

One disadvantage of galvanic technology is the use of lead as the anode element, as lead constitutes a hazardous waste, and thus may be difficult or expensive to dispose of.

Such galvanic cells are relatively large and expensive to manufacture, and are thus typically reused many times with different patients. For these reasons the semipermeable membrane and related connecting components used in galvanic cells increases the possibility of patient cross-contamination because of its reusable characteristics. Such use may span an entire year and perhaps thousands of different patients. Although such sensors can be sterilized between uses, such methods are relatively expensive and burdensome. As a result, such sensors are often not sterilized between each use.

Consequently, ventilators, anesthesia machines, or other oxygen delivery apparatus may be exposed to oxygen sensors which may have been contaminated by any number of previous patients. Clearly, such existing oxygen sensors pose a substantial risk of cross-contamination between patients. In addition to the danger of cross-contamination, some gases, such as nitrous oxide, can cause premature oxidation of the silver working electrode, resulting in decreasing cell sensitivity over extended periods of exposure.

Given the potential for cross-contamination with existing oxygen sensors, there is a great need for a single-use disposable oxygen sensor that can be manufactured inexpensively and that can be disposed of safely so as to be disposable after a single use. Such a single use sensor would completely eliminate the danger of cross-contamination posed by existing sensors. Such a single use sensor would also eliminate the problem of decreased sensitivity caused by exposure to certain anesthesia gasses.

It is accordingly an object of this invention to overcome the disadvantages and drawbacks of the known art and to provide a single-use disposable oxygen sensor for use in a wide variety of oxygen dispensing devices.

It is a further object of the present invention to provide single-use oxygen sensor that contains little or no environmentally hazardous materials so as to be easily and safely disposed of.

It is a further object of the present invention to provide a single-use oxygen sensor that is small in size and is, therefore, easily portable and can be incorporated unobtrusively in a variety of oxygen-dispensing devices.

Further objects and advantages of this invention will become apparent from the detailed description of a preferred embodiment which follows.

SUMMARY OF THE INVENTION

There is provided herein a method and apparatus for sensing a concentration of oxygen in a flow of gas in a breathing circuit for a patient. According to one embodiments a zinc-air cell is provided. A biasing voltage is provided across the zinc-air cell so that the zinc-air cell produces a current having a magnitude, wherein the magnitude of the current corresponds to the concentration of oxygen in the gas.

BRIEF DESCRIPTION OF THE DRAWINGS

Other objects, features, and advantages of the present invention will become more fully apparent from the following detailed description of the preferred embodiment, the appended claims, and the accompanying drawings in which:

DESCRIPTION OF THE PREFERRED EMBODIMENT(S)

The present invention is directed to oxygen sensors and methods for sensing the concentration of oxygen in a breathing circuit. In particular, a preferred oxygen sensor in accordance with the present invention can sense and identify concentrations of oxygen in a breathing circuit from 0% to 100%. Oxygen sensors in accordance with the present invention are relatively simple and inexpensive to manufacture and contain little or no hazardous waste. As a result, oxygen sensors according to the present invention are suitable for use in conditions where it is desirable to dispose of the sensor after only a single use. Moreover, oxygen sensors in accordance with the present invention are relatively small and can be incorporated into existing disposable parts of various breathing devices such as bacteria filters and oxygen tents.

Figure 1:
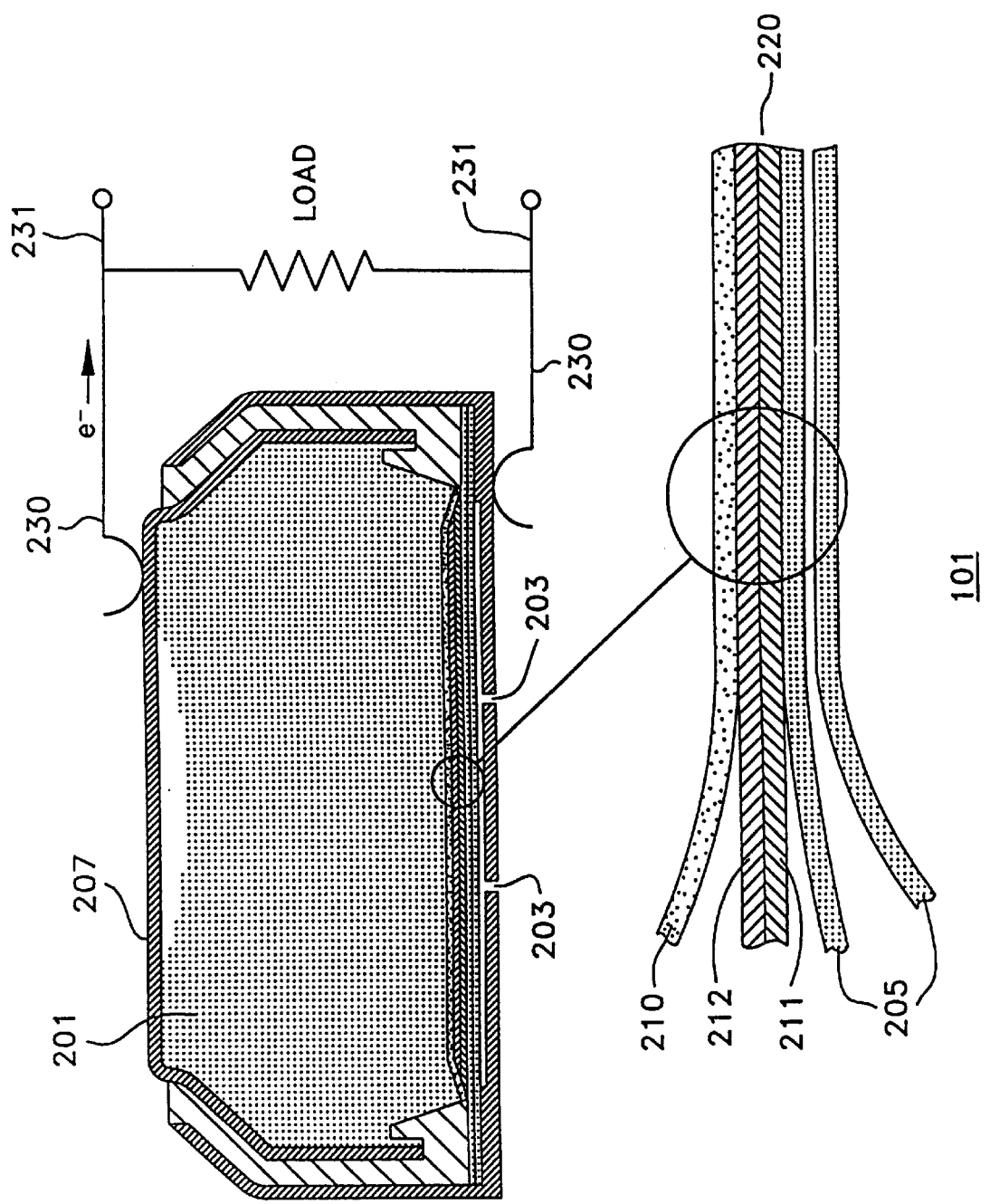
FIG. 1 shows a zinc-air cell in accordance with a preferred embodiment of the present invention.

Referring now to FIG. 1, there is shown zinc-air cell 101 in accordance with a preferred embodiment of the present invention. Cell 101 is a zinc-air battery, for example a 600 milliamp hour zinc-air battery. Cell 101 is a standard zinc-air battery comprising a zinc anode 201 in a casing 207 with atmospheric gas ports 203 to permit the entry of oxygen which acts as the cathode for cell 101. In a preferred embodiment of the present invention, cell 101 is modified by covering the atmospheric gas port 203 with a gas-permeable membrane 205. Membrane 205 may comprise two layers of film, as illustrated, for example, and restricts to the flow of oxygen to the zinc anode 201, thereby increasing the cell life.

As will be appreciated, the permeability of membrane 205 may be selected depending upon the amount of time anticipated between manufacture of cell 101 and use of cell 101 as an oxygen sensor. The less permeable the membrane, the slower the response time of cell 101 to oxygen. However, if membrane 205 is too permeable, the effect of interference gasses, i.e. various anesthesia gases such as nitrous oxide, will interfere with the accuracy of the sensor. In a preferred embodiment, membrane 205 is preferably a fluorocarbon film as TEFLON PFA™ film available from Dupont and is approximately one thousandth of an inch thick. As will be appreciated, such a cell will provide a current proportional to the oxygen concentration in which the cell is introduced when a proper biasing voltage is applied across the cell, as described in further detail hereinbelow.

As illustrated in FIG. 1, cell 101 in a preferred embodiment also comprises separator/barrier layer 210 and the active or catalytic layer 211, where the cathode reaction occurs, and which also comprises the current collector portion 212. As will be understood, the layers 205, 211, 212, and 210 are illustrated in FIG. 1 in enlarged blow-up portion 220. The "+" and "−" terminals of zinc-air cell 101 may be accessed by leads 230 which may be coupled to a load LOAD and coupled to a circuit at terminals 231.

Figure 2:
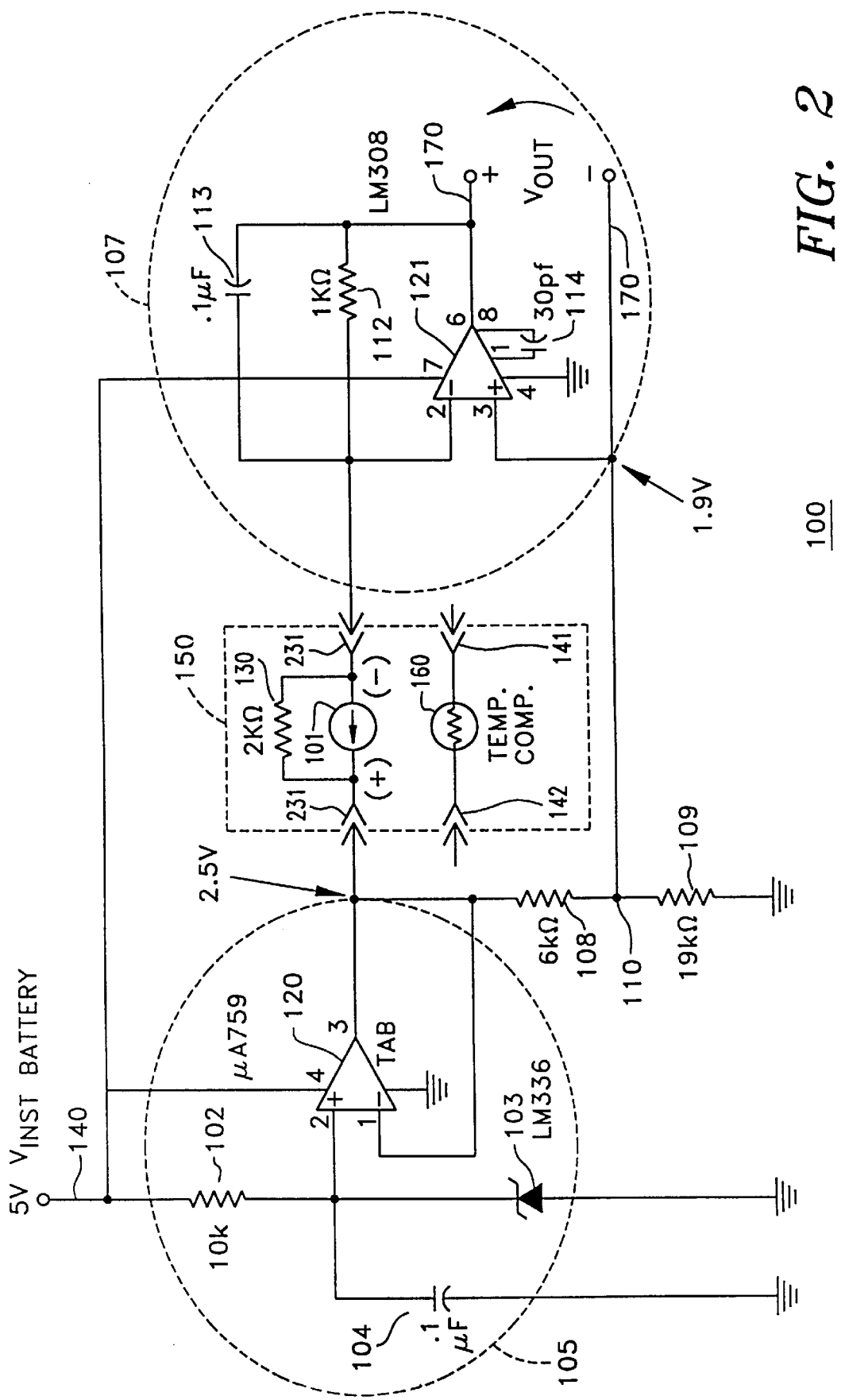
FIG. 2 shows a circuit incorporating the cell of FIG. 1 in accordance with a preferred embodiment of the present invention.

Referring now to FIG. 2, there is shown an oxygen sensor circuit 100 in accordance with the present invention. Oxygen sensor circuit 100 may be coupled to a modified zinc-air cell 101 at the "+" and "−" terminals 231 of zinc-air cell 101, as illustrated. In a preferred embodiment, cell 101, resistor 130, and thermistor 160 are physically located within a sensor unit 150 in a breathing circuit. The remainder of circuit 100 is preferably implemented within a portable analyzer device, which is connected via a cable at terminals 231 and 141 to cell 101, resistor 130, and thermistor 160.

Oxygen sensor circuit 100 biases zinc-air cell 101 so that the cell acts as a current source with a current output $I_{CELL}$, the magnitude of which is proportional to the concentration of oxygen ($O_2$) present at the cell. Circuit 100 also comprises means for converting the output current to a voltage in a usable range, as described in further detail hereinbelow.

Referring once more to FIG. 2, oxygen sensor circuit 100 comprises an input terminal 140 coupled to $V_{INST\ BATTERY}$, which in a preferred embodiment is a 5V source. Circuit 100 also comprises an output terminal 170. Output terminal 170 provides an output voltage $V_{OUT}$ which is directly proportional to the current output $I_{CELL}$, which is in turn related in a known manner to the oxygen concentration of the atmosphere around cell 101. As will be understood, in alternative preferred embodiments $V_{INST\ BATTERY}$ may be a voltage source having a voltage other than 5V, for example 3.3 volts for related 3.3-volt technology, with the values of components of circuit 100 modified accordingly.

As will be understood by those skilled in the art, in a preferred embodiment zinc-air cell 101 will provide an open circuit voltage of approximately 1.4V at ambient oxygen concentration of 20.9%, although other open circuit voltage characteristics are also possible for alternative preferred zinc-air cells, for example depending upon the characteristics of membrane 205. With these open circuit voltage parameters, when the voltage across zinc-air cell 101 is forced down and held to 600 mV by circuit 100 (i,e., "biased"), zinc-air cell 101 acts as a current source producing current $I_{CELL}$, wherein changes in oxygen concentration cause the current $I_{CELL}$ to vary proportionately with the oxygen concentration. Thus, a voltage impressed across the terminals of zinc-air cell 101 which forces it to act as a current source and to generate a current whose magnitude is related to the oxygen concentration is said to be a biasing voltage, which properly biases zinc-air cell 101 to function as an oxygen sensor. As described in further detail hereinbelow, circuit 100 converts the relative magnitude of current $I_{CELL}$ to a voltage $V_{OUT}$ which is therefore also proportional to the oxygen concentration.

Circuit 100 comprises a voltage reference buffer amplifier network 105, a voltage divider network comprising resistors 108 and 109, and current to voltage converter network 107. As will be understood, voltage reference buffer amplifier network 105 serves to provide a first reference voltage to the "+" terminal of cell 101. Voltage divider resistors 108, 109 and operational amplifier ("op amp") 121 provide a second reference voltage to the "−" terminal of cell 101. In a preferred embodiment, the first reference voltage is 2.5V, and the second reference voltage is 1.9V. Therefore, the voltage across zinc-air cell 101 is maintained at 600 mV, or approximately half the open circuit voltage of cell 101 at a nominal oxygen concentration of approximately 20.9%, as described above. This 600 mV bias voltage is selected, in a preferred embodiment, to be half of the open circuit cell voltage to allow cell 101 to respond from 0% to 100% oxygen concentration levels. Another reason for these preferred parameters is that it has been determined by the inventors that, in a preferred embodiment, 600 mV is the correct bias voltage to achieve the oxygen diffusion limiting current of cell 101, to achieve the new equilibrium of cell 101, as will be appreciated.

As illustrated in FIG. 2, buffer amplifier network 105 comprises a capacitor 104, a resistor 102, an op amp 120, and a voltage reference source 103, coupled as shown. As will be understood, voltage reference source 103 in a preferred embodiment is represented by a micropower low drift voltage reference diode 103, e.g. of type LM336. In a preferred embodiment, resistor 102 is 10 kΩ capacitor 104 is 0.1 $\mu$F, and voltage reference source 103 is a 2.5V reference source. Op amp 120 therefore provides 2.5V to the "+" terminal of cell 101. In a preferred embodiment, resistor 108 is 6 kΩ and resistor 109 is 19 kΩ. As will be understood, in alternative referred embodiments resistor 109 may be a potentiometer so that its resistance may be easily varied for fine tuning the biasing and operation of circuit 100. Current to voltage converter network 107 comprises op amp 121, feedback resistor 112, and compensation capacitor 113, intercoupled as shown. In a preferred embodiment, compensation capacitors 113 and 114 are 0.1 $\mu$F and 30 pF, respectively, and feedback resistor 112 is 1 kΩ. Voltage divider network 108, 109 in a preferred embodiment maintains a voltage of approximately 1.9V at its centertap node 110, which thus is the voltage at the "−" terminal of zinc-air cell 101 because of the virtual ground connection across the differential inputs of op amp 121. These elements as incorporated in circuit 100 therefore serve as a means for supplying the second reference voltage of 1.9V to the "−" terminal of cell 101. Thus, a voltage of approximately 600 mV is maintained across cell 101. As will be appreciated, in circuit 100 zinc-air cell 101 is not ground referenced to ensure the error free measurement of small signals.

Current-to-voltage converter network 107 serves to convert the relative magnitude of current $I_{CELL}$, into an output voltage $V_{OUT}$ which varies within a usable range. In a preferred embodiment, $V_{OUT}$ ranges from approximately 1.5V to 2V, where 1.5V corresponds to 0% oxygen and 2V corresponds to 100% oxygen concentration. Thus, the output voltage range is suitable for analog to digital ("A/D") conversion by standard 3.3V A/D converters, as will be appreciated by those skilled in the art. It will be understood by those skilled in the art that a wide variety of circuit configurations may be employed to convert the current $I_{CELL}$ produced by zinc-air cell 101 to an analog output voltage $V_{OUT}$ readable by devices such as standard voltmeters or A/D converters.

As will be appreciated, zinc-air cell 101 may be utilized to measure the oxygen concentration in a gas sample as follows. First, cell 101 is introduced into or otherwise exposed to a gas sample, for example in a breathing circuit. Oxygen present in the sample causes cell 101 to produce a current, when cell 101 is properly biased by circuit 100. Circuit 100 converts the current to a voltage with standard current to voltage conversion circuitry, as discussed above with reference to FIG. 2. This current to voltage conversion is configured to yield an output voltage in a predetermined range. To enable the sensor to measure oxygen concentrations from 0% to 100%, cell 101 is preferably biased such that at least a minimal voltage output is produced by the current to voltage converter, in response to a corresponding minimal current output by the cell, when the gas sample has 0% oxygen. Thus, as described hereinabove, in a preferred embodiment of the present invention, cell 101 is biased to approximately 600 mV.

This is accomplished in usage of cell 101 for an oxygen reading by first deep discharging cell 101 by connecting a relatively low-resistance resistor intermittently across the cell with a pulse width modulated signal at a discharge of no greater than 600 mA. In one embodiment such discharging takes approximately 2 seconds, and may be accomplished by the analyzer unit which contains circuit 100 disconnecting cell 101 via its terminals 231 from circuit 100 temporarily and attaching cell 101 to circuitry sufficient to deep discharge the cell. Cell 101 is then re-coupled to circuit 100 and after a small time-out period, for example 5 seconds, the analyzer device may check the open-circuit voltage of cell 101 to ensure that it has reached 600 mV within the requisite time. At this point, the cell is biased and is presumably outputting a current proportional to the $O_2$ concentration, which is being continually converted to a related voltage $V_{OUT}$ by circuit 100. Thus, once this bias is achieved, appropriate circuitry within the analyzer, such as an A/D converter and an appropriately programmed microprocessor or application-specific integrated circuit ("ASIC"), may be used to convert $V_{OUT}$ to a digital voltage which is then converted to an $O_2$ reading. This latter conversion may utilize, as will be appreciated, lookup tables ("LUTs") or other techniques that correlate the voltage $V_{OUT}$ with the $O_2$ concentration in accordance with the known relationships between $O_2$ concentration and the current $I_{CELL}$ generated by cell 101 for given concentrations of $O_2$.

Figure 3:
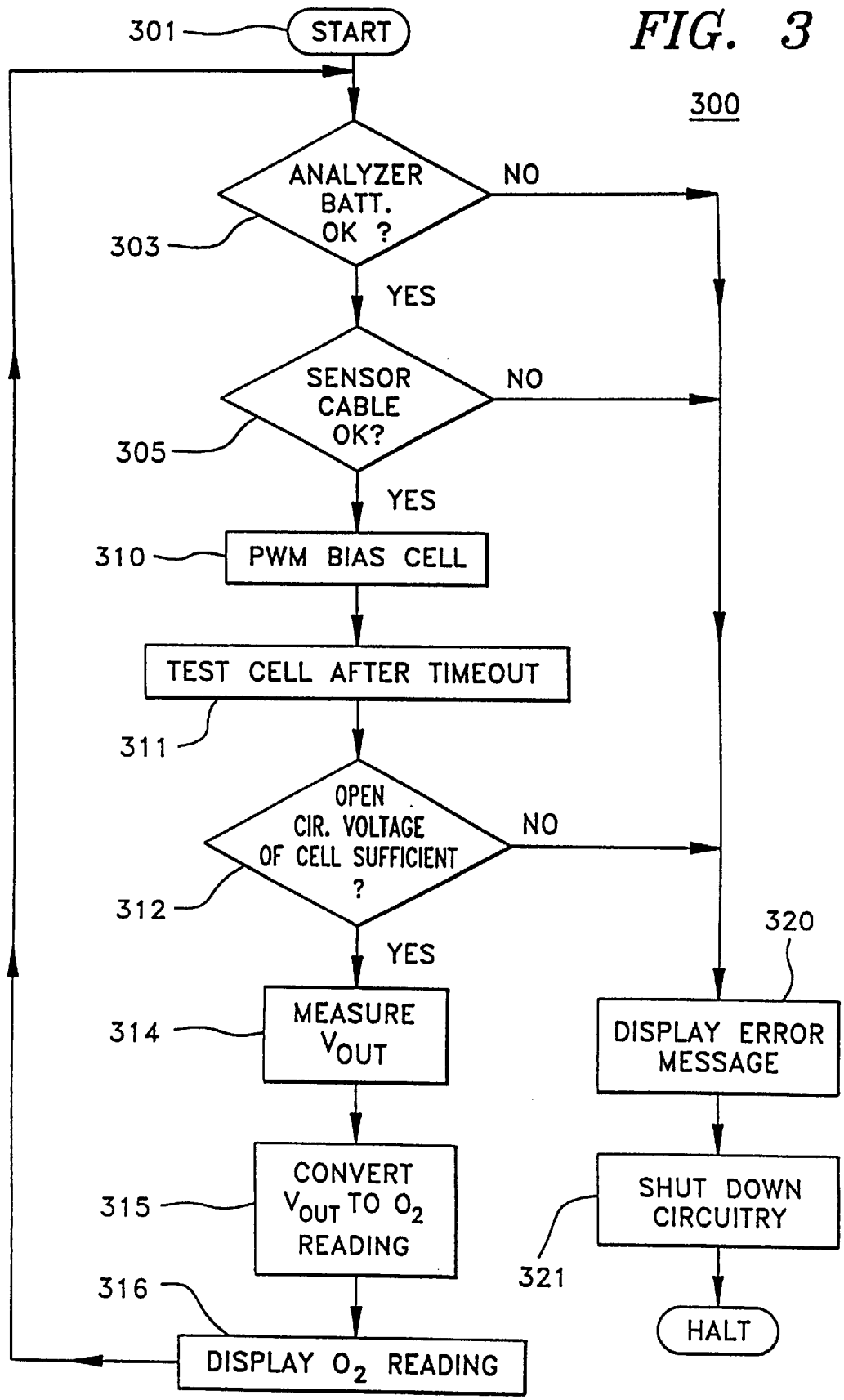
FIG. 3 shows a flow diagram of the steps of a method for sensing the concentration of oxygen in a gas sample utilizing the circuit of FIG. 2.

Referring now to FIG. 3, there is shown a flow diagram 300 illustrating in more detail a method for sensing the concentration of oxygen in a gas sample utilizing the circuit 100 of FIG. 2, in conjunction with a computer monitoring the output voltage $V_{OUT}$ of circuit 100, and displaying relevant information to a user on a display. For example, the computer and relevant programming and circuitry and display may be contained in a remote analyzer device. This device may contain circuitry 100 as well, and is coupled via a cable to sensor unit 150 FIG. 2. As an example, a breathing apparatus incorporating sensor unit 150 may be attached to a patient's body and is connected via a cable to the analyzer which is hanging on an intravenous ("IV") pole a few feet away.

As shown in step 303, a test is first made of the battery powering the analyzer device, including supplying the power supply for circuitry 100. If the battery voltage is not within operational limits, an appropriate error message (such as a "low battery" icon) may be displayed on the analyzer device's display, and circuitry 100 shut down (steps 303, 320, 321). If the battery voltage is within operational limits, then the sensor cable is tested (step 305). If the cable connection is not satisfactory then an appropriate error message (such as a "bad cable" icon) may be displayed on the analyzer device's display, and circuitry 100 shut down (steps 305, 320, 321).

Next, the analyzer tests whether cell 101 is operational. This is done by first deep discharging cell 101, as described above, and then testing the open-circuit voltage of cell 101 at a point in time later by which time cell 101 should have risen to 600 mV from its deep discharged state. Thus, cell 101 is first deep discharged by intermittently coupling it in parallel with a relatively small resistor in accordance with pulse-width modulation, as described above (step 310). This step may take 2 seconds in one embodiment. After a sufficient timeout has elapsed, cell 101 is tested (step 311). If the open circuit voltage of cell 101 is not sufficient, for instance if its open circuit voltage is more than a predetermined threshold voltage below 600 mV, then an appropriate error message (such as a "change sensor unit" icon) may be displayed on the analyzer device's display, and circuitry 100 shut down (steps 312, 320, 321). Otherwise, a reading is taken of $V_{OUT}$, which is converted to a digital signal from which the $O_2$ concentration is interpreted by the processor in accordance with the characteristics of cell 101 as biased by circuit 100 (steps 314, 315). As will be understood, the output voltage $V_{OUT}$ may be read with a voltage sensor comprising an A/D converter calibrated to the output voltage range. The $O_2$ reading so computed is then displayed (step 316), and the process repeated.

As will be understood by those skilled in the art, in alternative preferred embodiments, when the open circuit voltage of cell 101 in step 311 is less than 600 mV but within a tolerable range below or above 600 mV, then this difference may be taken into account by the processor of the analyzer in converting $V_{OUT}$ to an $O_2$ reading. As will further be understood by those skilled in the art, temperature variations may affect the manner in which cell 101 responds to changes in $O_2$ concentration over temperature. Thus, thermistor 160 may be utilized to provide the analyzer with the temperature so that temperature variations in cell 101's performance may be taken into account by the analyzer when converting $V_{OUT}$ to an $O_2$ reading. It will further be understood that after reaching step 316 steps 314–316 may be repeated in a loop to continually display an $O_2$ reading for a given period of time.

Since the current of cell 101 is approximately 10 $\mu$A per percent $O_2$, the voltage gain of current to voltage converter 107 must be kept to a minimum to stay within the common mode range of op amp 121. In addition, this will allow the use of a 3.3V technology 8-bit microprocessor A/D converter. With a 100% full scale $O_2$ reading, the input voltage will be 1 volt, which will easily resolve +/–1% $O_2$.

An oxygen sensor in accordance with the present invention may be incorporated into a variety of disposable medical devices. For example, an oxygen sensor in accordance with the present invention may be incorporated into a disposable bacteria filter for use in anesthesia and ventilator circuits. Alternatively, an oxygen sensor in accordance with the present invention may be incorporated into a disposable oxygen tent.

Figure 4:
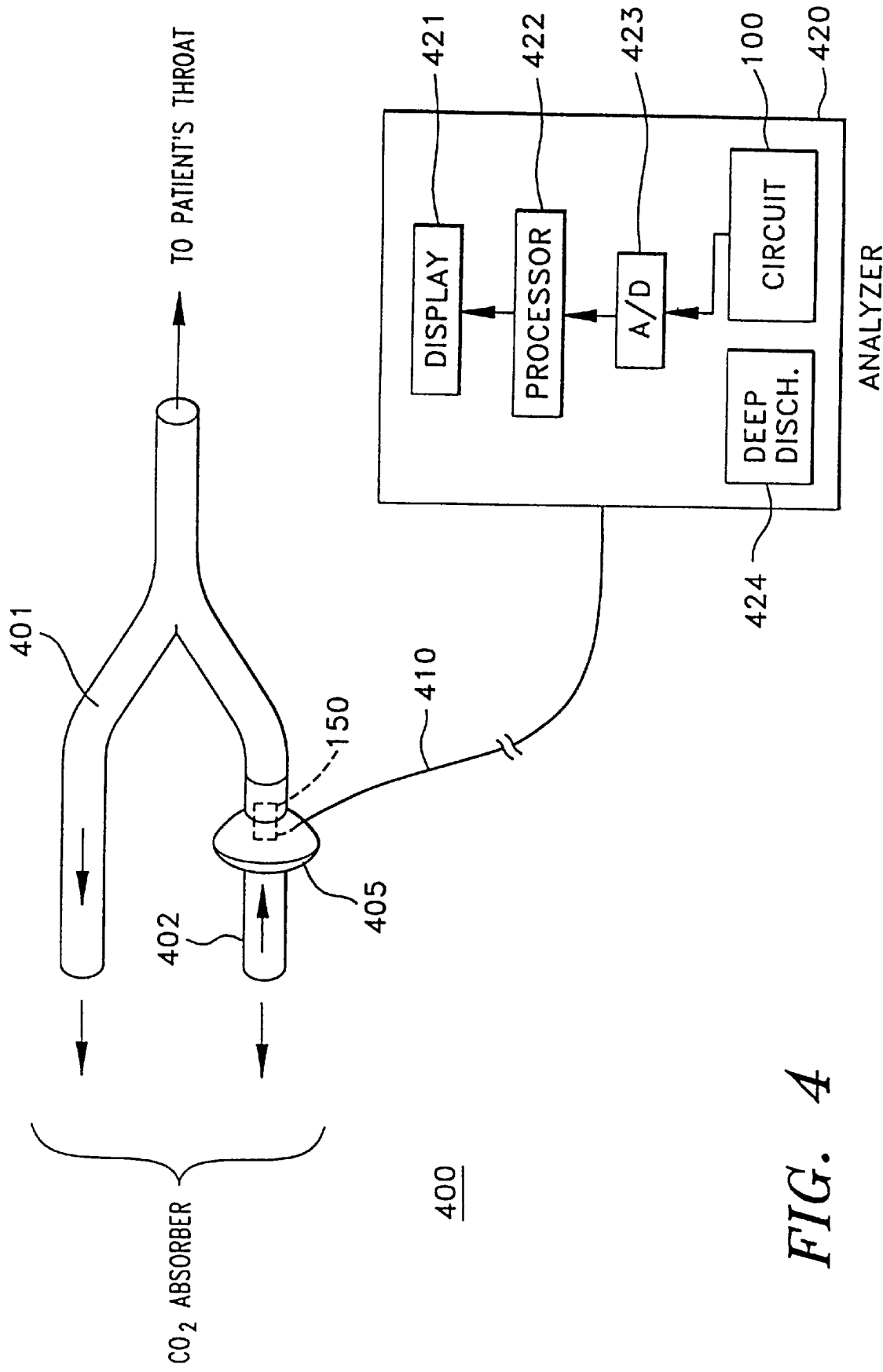
FIG. 4 illustrates a breathing circuit incorporating the zinc-air cell of FIG. 1 and coupled to the circuit of FIG. 2, in accordance with a preferred embodiment of the present invention.

Referring now to FIG. 4, there is illustrated a breathing circuit 400 incorporating zinc-air cell 101 of FIG. 1 and coupled to circuit 100 of FIG. 2, in accordance with a preferred embodiment of the present invention. Breathing circuit 400 comprises tubing having both inspiratory and expiratory limbs 402 and 401, respectively. The gas respirated by a patient is communicated via these limbs to a $CO_2$ absorber. This device, as will be understood, removes $CO_2$ from the patient's exhalations, and mixes breathable air with other gases such as anaesthetics and delivers it via inspiratory limb 402 to the patient. Typically this passes through a bacteria filter 405. To ensure that the right amount of oxygen is being delivered to the patient, it is important to be able to determine the $O_2$ concentration delivered to the patient in this inspiratory limb. Sensor unit 150 is preferably placed on the patient side of bacteria filter 405 to be closer to the patient to minimize error due to tube leakage. Sensor unit 150's components cell 101 and resistor 130, and thermistor 160, are coupled at their respective terminals 231, 141 via cable 410 to analyzer 420.

As will be appreciated, sensor unit 150 may be provided within bacteria filter 405 as a single unit or within a suitable piece of housing couplable to bacteria filter 405. Thus, sensor unit 150 may be incorporated in a segment or portion of breathing circuit 400 and couplable thereto. For example, a medical professional may physically couple a bacteria filter 405 having a built-in sensor unit 150 to the inspiratory limb 402 of breathing circuit 400, such that the bacteria filter forms a part of the breathing circuit 400 and such that the gas flowing to the patient via the inspiratory limb 402 flows across the bacteria filter of bacteria filter 402 and also around sensor unit 150.

This analyzer 420 comprises circuitry 100, A/D converter 423, processor 422, and display 421. Analyzer 420 also comprises deep discharging circuitry 424 sufficient to deep discharge cell 101 as described hereinabove. Analyzer 420 also comprises sufficient switching means to couple cell 101 via cable 410 as necessary to deep discharger 424, circuit 100, and the like.

It will be further understood that various changes in the details, materials, and arrangements of the parts which have been described and illustrated in order to explain the nature of this invention may be made by those skilled in the art without departing from the principle and scope of the invention as expressed in the following claims.

What is claimed is:

1. An apparatus for sensing oxygen concentration comprising:

(a) a zinc-air cell having a pair of electrodes adapted to be exposed to, and activated by, a gaseous atmosphere;

(b) a circuit connected across the electrodes of the zinc-air cell;

(c) means, within said circuit and connected to the electrodes of the zinc-air cell, for automatically maintaining the potential difference between said electrodes of the zinc-air cell at a level such that for any oxygen concentration in a gaseous atmosphere to which the zinc-air cell is exposed, from 0% oxygen to 100% oxygen, there is a corresponding current in the zinc-air cell; and (d) means, connected to said circuit, for measuring the current in the zinc-air cell over the entire range of said current.

2. Apparatus according to claim 1, in which said means for automatically maintaining the potential difference between said electrodes, holds said potential difference at a constant level.

3. Apparatus according to claim 1, in which said means for automatically maintaining the potential difference between said electrodes, holds said potential difference at 600 millivolts.

4. Apparatus according to claim 1, including a breathing circuit for a patient, the breathing circuit having an inspiratory limb for the flow of gas therethrough, and in which the zinc-air cell is located within the inspiratory limb of the breathing circuit.

5. Apparatus according to claim 4, in which said means for automatically maintaining the potential difference between said electrodes, holds said potential difference at a constant level.

6. Apparatus according to claim 4, in which said means for automatically maintaining the potential difference between said electrodes, holds said potential difference at 600 millivolts.

* * * * *